United States Patent
Klemm

(10) Patent No.: US 7,658,711 B2
(45) Date of Patent: Feb. 9, 2010

(54) ENDOSCOPE, IN PARTICULAR FOR TRACHEOTOMY

(75) Inventor: Eckart Klemm, Dresden-Ockerwitz (DE)

(73) Assignee: Karl Storz GmbH & Co. KG (DE)

( * ) Notice: Subject to any disclaimer, the term of this patent is extended or adjusted under 35 U.S.C. 154(b) by 393 days.

(21) Appl. No.: 11/438,838

(22) Filed: May 23, 2006

(65) Prior Publication Data

US 2006/0270907 A1    Nov. 30, 2006

(30) Foreign Application Priority Data

May 27, 2005   (DE)   .................. 20 2005 008 788 U

(51) Int. Cl.
*A61B 1/07*   (2006.01)
*A61B 1/06*   (2006.01)

(52) U.S. Cl. .................. 600/182; 600/178; 600/177; 600/171; 600/120; 600/129

(58) Field of Classification Search .................. 600/120, 600/129, 130, 182, 170, 171, 177, 178
See application file for complete search history.

(56) References Cited

U.S. PATENT DOCUMENTS

| 2,797,683 | A | * | 7/1957 | Aiken | 600/184 |
|---|---|---|---|---|---|
| 4,567,882 | A | * | 2/1986 | Heller | 600/249 |
| 4,576,147 | A | * | 3/1986 | Hashiguchi | 600/129 |
| 4,620,547 | A | * | 11/1986 | Boebel | 600/567 |
| 4,685,451 | A | * | 8/1987 | Ando | 600/181 |
| 4,697,577 | A | * | 10/1987 | Forkner | 600/173 |
| 4,757,819 | A | * | 7/1988 | Yokoi et al. | 600/156 |
| 4,838,247 | A | * | 6/1989 | Forkner | 600/173 |
| 5,170,774 | A | * | 12/1992 | Heckele | 600/128 |
| 5,280,788 | A | * | 1/1994 | Janes et al. | 600/476 |
| 5,538,497 | A | * | 7/1996 | Hori | 600/182 |
| 5,588,952 | A | * | 12/1996 | Dandolu | 600/249 |
| 5,700,236 | A | * | 12/1997 | Sauer et al. | 600/175 |
| 5,782,751 | A | * | 7/1998 | Matsuno | 600/157 |
| RE36,434 | E | * | 12/1999 | Hamlin et al. | 600/109 |
| 6,537,209 | B1 | * | 3/2003 | Pinkhasik et al. | 600/170 |

FOREIGN PATENT DOCUMENTS

| DE | 695 27 958 T2 | 5/2003 |
|---|---|---|
| EP | 0 762 906 B1 | 8/2002 |

* cited by examiner

*Primary Examiner*—John P Leubecker
(74) *Attorney, Agent, or Firm*—St. Onge Steward Johnston & Reens LLC

(57) ABSTRACT

An endoscope, comprising an elongated tubular shaft for introducing into a body of a patient, the shaft having a longitudinal axis and a distal end, and further having an opening the distal end. A light guide is arranged along the shaft and has a light-emitting distal end, the light-emitting distal end being arranged in the area of the opening of the shaft in order to radiate light from the opening.

17 Claims, 5 Drawing Sheets

ENDOSCOPE, IN PARTICULAR FOR TRACHEOTOMY

BACKGROUND OF THE INVENTION

The invention relates to an endoscope.

Without limiting its general application, the endoscope according to the invention is particularly suitable for tracheotomy. An endoscope used for this purpose is also referred to as a tracheoscope or bronchoscope.

In a tracheotomy procedure, when a patient whose normal breathing through the nose and mouth is impaired or no longer possible, an artificial route of respiration is established through the throat below the larynx. To do this, a trocar is used to create, from the outside, an incision through the throat and into the trachea, into which a tracheotomy cannula is later inserted through which the patient then breathes or can be ventilated.

A difficulty that arises in an operation of this kind lies in determining the exact position of the incision for the subsequent tracheotomy cannula. For this purpose, as has been described in document DE 695 27 958 T2; an endoscope is introduced through the patient's mouth and into the trachea, where the distal end of the shaft of the endoscope comes to lie just below the larynx. Arranged in the known endoscope there is a light guide whose distal end, from a distal opening of the endoscope shaft, radiates light in the direction of the anterior wall of the trachea. A spot of light is then visible on the skin of the front area of the throat, and the illuminated area of the trachea is also made visible. By moving the endoscope or light guide, the light spot can now be positioned in such a way that it comes to lie between two cricoid cartilages or tracheal rings of the trachea. The cricoid cartilages or tracheal rings stand out from the rest of the tracheal wall by virtue of a different intensity or coloration of the light spot. As soon as the light spot is correctly positioned, the aforementioned incision through the skin and into the trachea can now be made by means of a trocar with the aid of the light spot.

The known endoscope has a light guide which is continuously straight and whose light-emitting window is cut obliquely in relation to the longitudinal axis of the light guide. This results in an obtuse angle of radiation of the light relative to the longitudinal axis of the light guide. Since the light is not radiated strictly to form a point but instead in an areal manner, the oblique incidence of light on the tracheal wall has the effect that the visible light spot is "smudged". To ensure a perpendicular incidence of the beam of light on the tracheal wall, the known endoscope has to be held obliquely relative to the longitudinal axis of the trachea, but the confined spaces in the region of the larynx and mouth through which the endoscope is introduced means this is not possible. If the light spot visible from outside is smudged, however, the incision into the trachea for the subsequently inserted tracheotomy cannula cannot be made with pinpoint precision. If this incision is not formed with pinpoint precision, the result of the tracheotomy may be compromised.

SUMMARY OF THE INVENTION

An object of the invention is therefore to develop an endoscope of the type mentioned at the outset in such a way that it allows an incision to be made into the trachea with pinpoint precision.

According to the invention, an endoscope is provided, comprising an elongated tubular shaft for introducing into a body of a patient, the shaft having a longitudinal axis and a distal end, and further having an opening at the distal end. A light guide is arranged along the shaft and has a light-emitting distal end, the light-emitting distal end being arranged in the area of the opening of the shaft in order to radiate light from the opening. The light-emitting distal end of the light guide is angled relative to the longitudinal axis of the shaft by an angle in a range of about 70° to about 110°.

The angled arrangement, according to the invention, of the light-emitting distal end of the light guide relative to the longitudinal axis of the shaft means that the light is also radiated at an angle in the range of about 70° to about 110° relative to the longitudinal direction of the shaft, so that, even without the shaft of the endoscope being positioned obliquely, it is possible to produce, on the tracheal wall and on the skin of the throat area, a smaller light spot than is obtained merely with an obliquely configured window at the distal end of the light guide. Thus, the endoscope shaft can be introduced advantageously in the longitudinal direction of the trachea and does not have to be angled relative to the trachea. In this way, the advantage of pinpoint precision of the incision into the trachea at the desired site is achieved.

In a preferred embodiment, a light-emitting window of the light-emitting end of the light guide extends approximately parallel to the longitudinal axis of the shaft when the light guide is oriented parallel to the longitudinal axis of the shaft.

With a light-emitting window extending parallel to the longitudinal axis of the shaft, the light spot produced on the tracheal wall and on the skin in the throat area becomes even smaller and the incision into the trachea can therefore be made with even greater precision, because the incidence of the light beam is at least approximately perpendicular to the skin. By contrast, in the case of an oblique light-emitting window, as in the known endoscope, there is an inevitable smudging and increase in size of the light spot, which makes an incision with pinpoint accuracy difficult.

In another preferred embodiment, the distal end of the light guide is angled relative to the longitudinal axis of the shaft by an angle in a range of about 80° to about 180°, and in yet another preferred embodiment the light-emitting distal end of the light guide is angled relative to the longitudinal axis of the shaft by an angle of about 90°.

Especially by combination of a distal end of the light guide, set at a right angle, with a window which extends parallel to the longitudinal axis of the shaft and from which the light emerges, it is possible to produce a particularly small and sharp light spot on the tracheal wall and on the skin in the throat area, with the result that the formation of the incision can be effected with very great accuracy.

According to another aspect of the invention, an endoscope is provided, comprising an elongated tubular shaft for introducing into a body of a patient, the shaft having a longitudinal axis and a distal end, and further having an opening at the distal end. The opening of the shaft extends obliquely relative to the longitudinal axis of the shaft. A light guide is arranged along the shaft and has a light-emitting distal end, the light-emitting distal end being arranged in the area of the opening of the shaft in order to radiate light from the opening.

Preferably, an edge of the opening forms, with the longitudinal axis of the shaft, an angle in a range of about 10° to about 40°.

The surface area of the opening is increased by this strongly oblique positioning of the opening of the shaft relative to the longitudinal axis of the shaft. The increase in the surface area of the opening now has the advantage that the rear wall of the shaft is likewise increased in size in the area of the opening, and this results in an enlarged protective surface which, during insertion of the trocar into the trachea, advantageously avoids the trocar drilling through or damaging the opposite wall of the trachea. Also in the subsequent maneuvers involved in fitting the tracheotomy cannula in which instruments are inserted through the incision into the trachea, the rear wall of the shaft, increased in size by the aforementioned measure in the area of the opening, advantageously serves as protection against damage to the posterior wall of the trachea.

In this context, it is preferable and advantageous if the light-emitting distal end of the light guide is arranged or comes to lie in a proximal area of the opening when the light guide is inserted into the shaft.

It is particularly preferable if the edge of the opening forms, with the longitudinal axis of the shaft, an angle in a range of about 15° to about 25°.

In another preferred embodiment, the light guide is arranged or can be arranged in the interior of the shaft, and the light guide extends near a shaft wall which is directed away from the opening.

This measure has the advantage that the light guide as a whole can be made rigid and, despite the angled position of the light-emitting distal end, the diameter of the shaft of the endoscope is not greater than in conventional endoscopes of this kind.

In another preferred embodiment, the distal end of the light guide has such a length that it does not protrude from the opening.

The advantage of this is that, if the endoscope is introduced into the patient's body already together with the light guide, the light-emitting distal end of the light guide does not form an obstacle during the advance of the endoscope.

In another preferred embodiment, the light guide can be withdrawn from the shaft.

This measure has the advantage of improved cleaning of the endoscope, since the light guide, after withdrawal from the shaft of the endoscope, can be more thoroughly cleaned than if it were to be left in the shaft of the endoscope. Moreover, in some cases the light guide is not required for the whole operation, so that, after removal of the light guide, the shaft of the endoscope can be used for the insertion of other instruments, or of a traction wire used in the tracheotomy procedure, without the light guide forming an obstacle.

In another preferred embodiment, a coupling is present at the proximal end of the light guide and at the proximal end of the shaft for the purpose of securing the light guide on the shaft in a predetermined position of rotation of the light guide relative to the shaft.

In conjunction with the angled positioning of the light-emitting distal end of the light guide, this measure has the advantage that the light guide is always connected to the shaft in the correct position of rotation in relation to the opening of the shaft, such that the light-emitting distal end of the light guide faces toward the opening.

Further advantages and features will become evident from the following description and from the attached drawing.

It will be appreciated that the aforementioned features and the features still to be explained below can be used not only in the respectively cited combination, but also in other combinations or alone, without departing from the scope of the present invention.

BRIEF DESCRIPTION OF THE DRAWINGS

An illustrative embodiment of the invention is described in more detail below with reference to the drawings, in which.

DETAILED DESCRIPTION OF THE INVENTION

Figure 1:
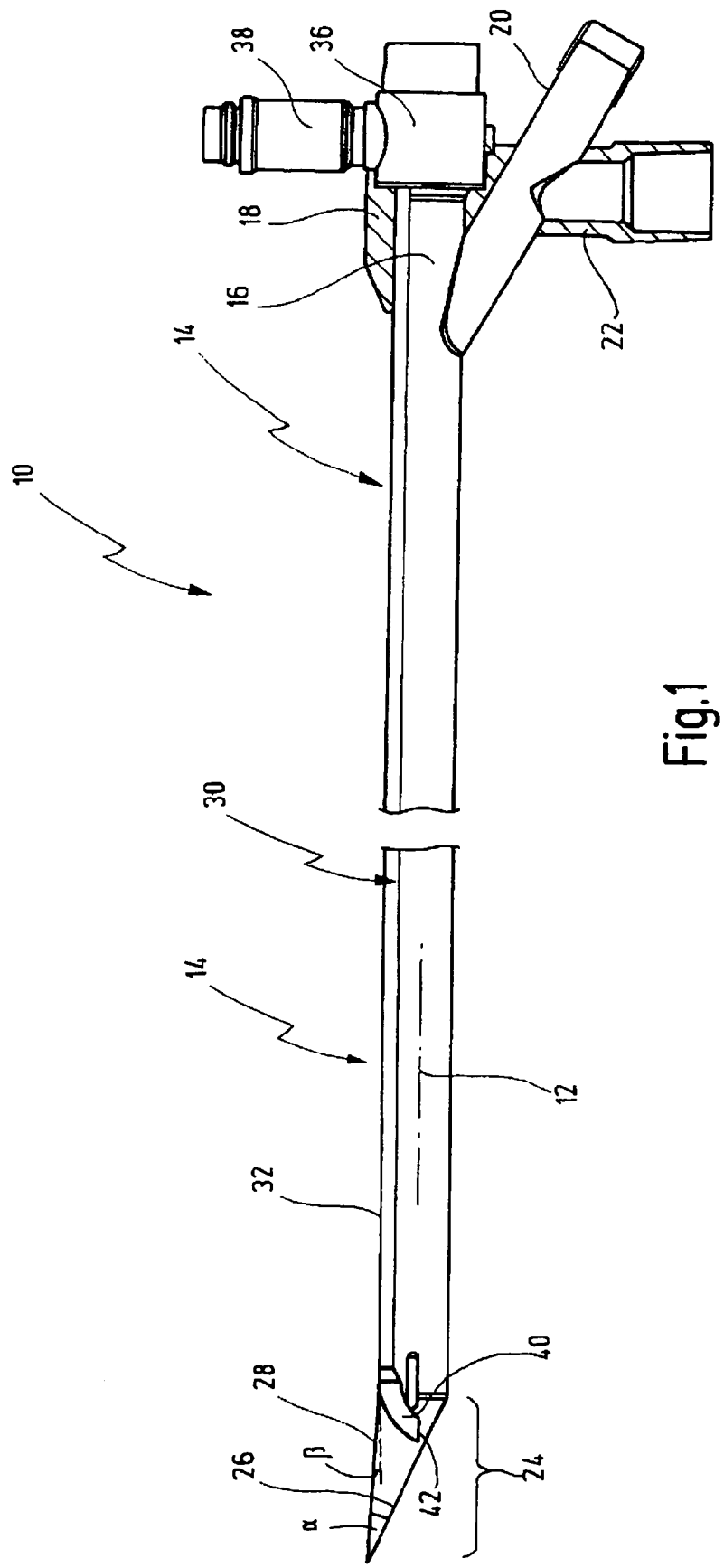
FIG. 1 shows an endoscope in a side view and partially in longitudinal section.
Figure 4:
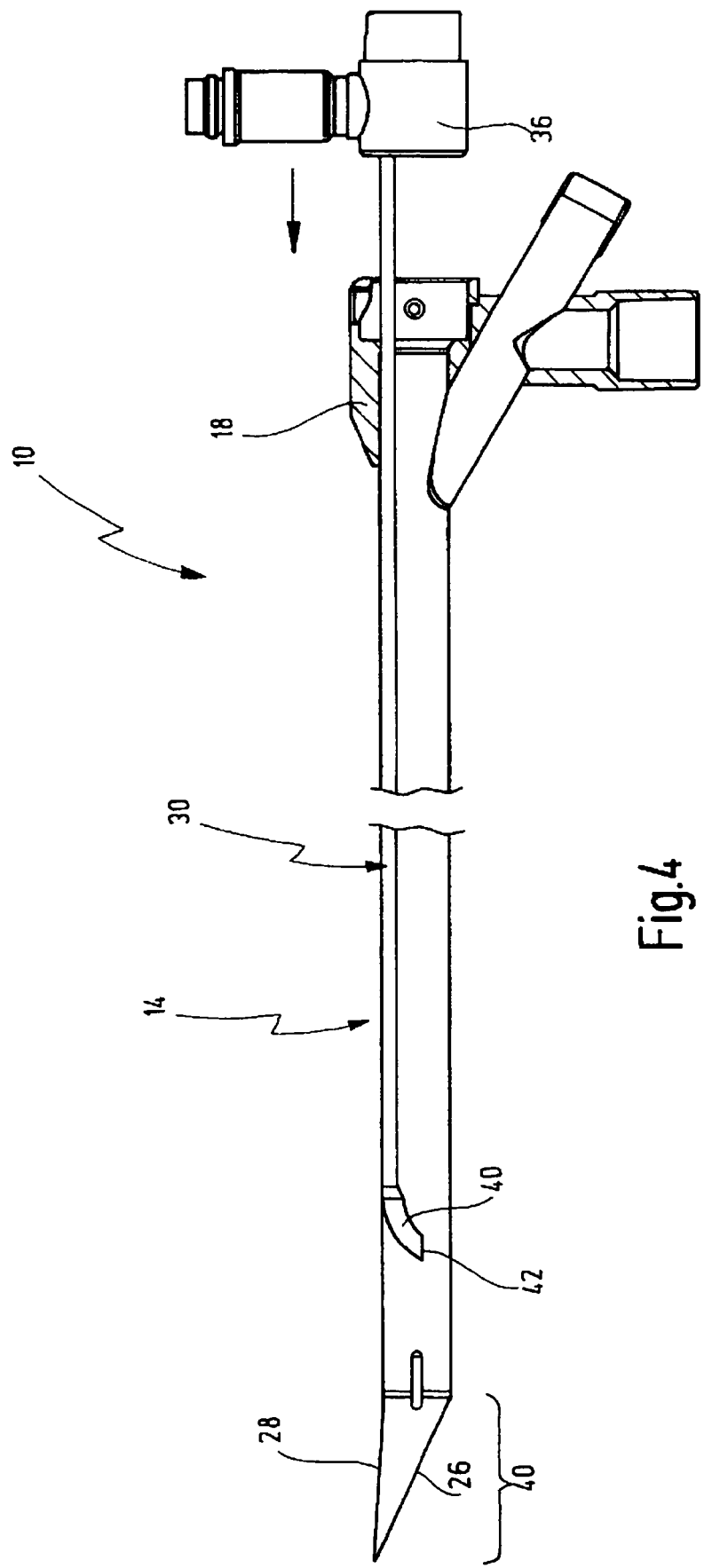
FIG. 4 shows a side view of the endoscope from FIG. 1, the light guide having been inserted into the shaft of the endoscope.

In FIGS. 1 and 4, an endoscope for tracheotomy is provided with the general reference number 10. It will be appreciated that the endoscope 10 can also be used in other medical disciplines.

Figure 2:
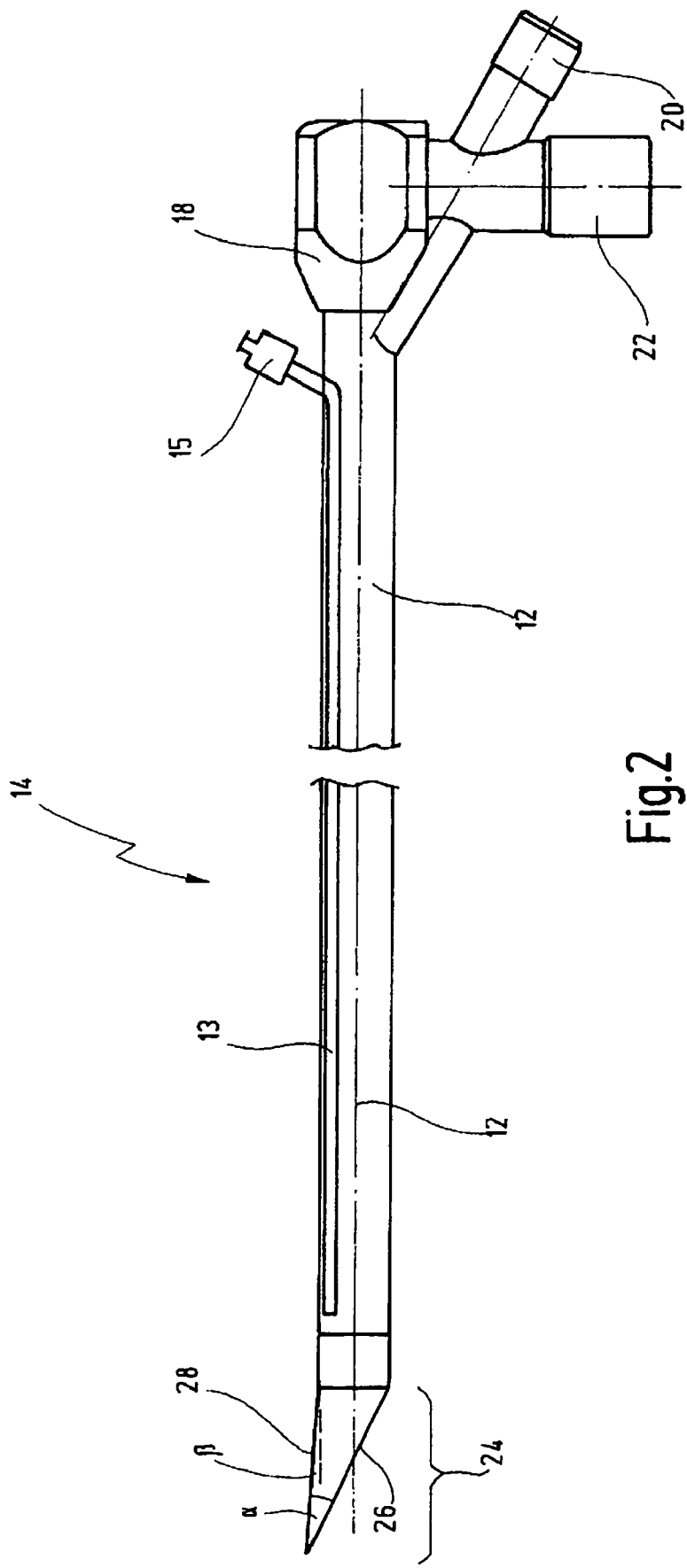
FIG. 2 shows a shaft of the endoscope from FIG. 1 in a side view, with associated attachment parts at the proximal end of the shaft.
Figure 3:
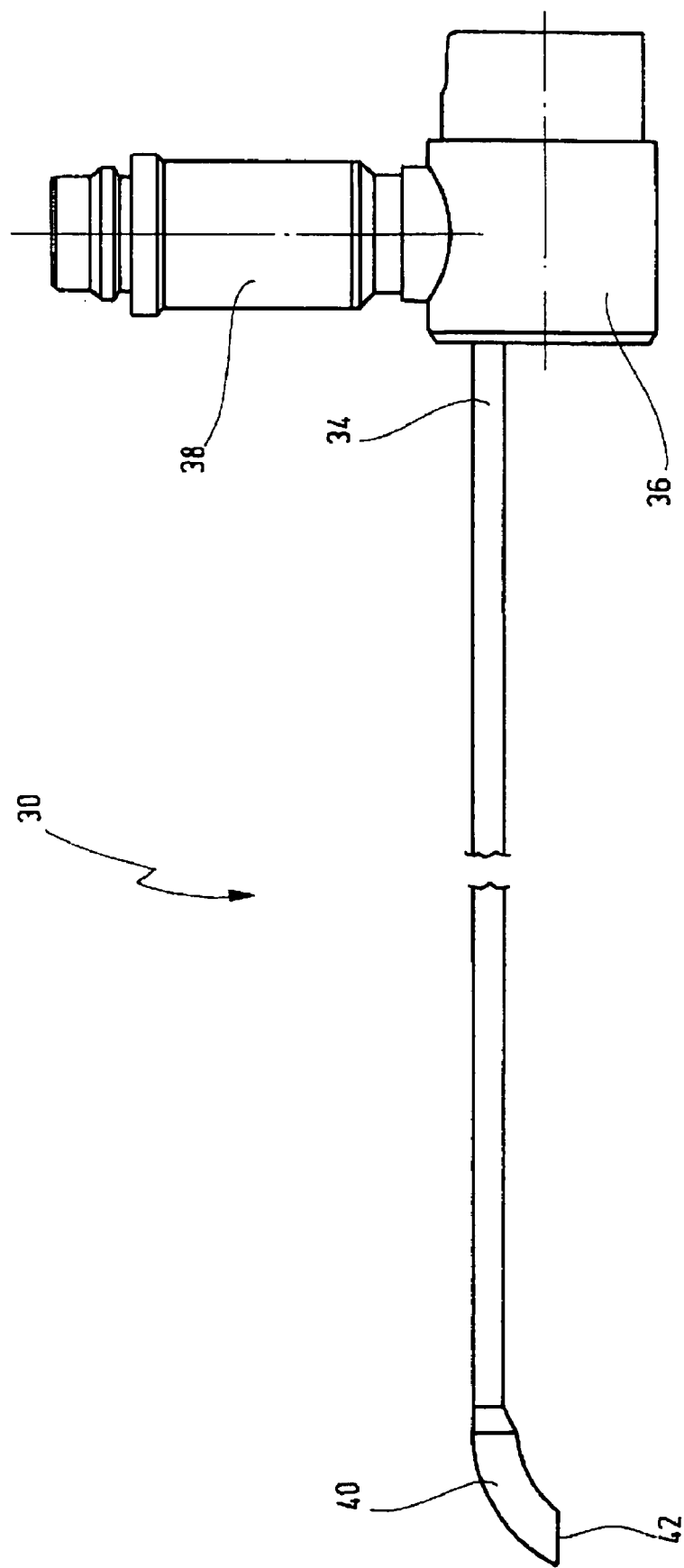
FIG. 3 shows a side view of a light guide of the endoscope from FIG. 1 on its own, with associated attachment parts at the proximal end of the light guide, the light guide in FIG. 3 being shown enlarged by comparison with FIG. 1.

Components of the endoscope 10 are shown separately in FIGS. 2 and 3.

The endoscope 10 comprises a shaft 14 which has a longitudinal axis 12 and which, because of its length, is shown interrupted in the figures. The shaft 14 is in particular rigid. The longitudinal axis 12 is to be understood as the direction of longitudinal exension of the shaft 14.

At a proximal end 16, the shaft 14 has a coupling part 18 which will be described later and which is used to secure a light guide of the endoscope 10; a connector tube 20 which extends obliquely and is used for the insertion of auxiliary instruments, wires and the like; and a connector tube 22 which can be used, for example, for attachment of a ventilation line in the event of the endoscope 10 being used in a tracheotomy. FIG. 2, which shows the shaft 14 separately, also indicates a channel 13 arranged on the outside of the shaft 14 and with a connector 15 for attachment of a line (not shown). The outer channel 13, which has been left out in FIGS. 1 and 4, is used for respiratory gas monitoring.

At the distal end, the shaft 14 has an opening 24 at which the shaft 14 opens out. An edge 26 of the opening 24 extends obliquely in relation to the longitudinal axis 12 of the shaft 14 and forms, with the longitudinal axis 12 of the shaft 14, an angle α in the range of about 10° to about 40°; in the present illustrative embodiment about 20°.

A rear wall 28 of the shaft 14, directed away from the opening 24, is closed and extends over more than approximately half the circumference of the shaft 14. The central surface line of the rear wall 28 as seen in FIG. 1 is slightly oblique in relation to the rest of the wall of the shaft 14 and in relation to the longitudinal axis 12 of the shaft 14 by an angle β, specifically pointing outward by a few degrees.

The endoscope 10 also comprises a light guide 30, which is shown separately and on an enlarged scale in FIG. 3.

The light guide 30 in FIG. 1 is arranged along the shaft 14, specifically in the interior of the shaft 14, near a wall 32 of the shaft 14 directed away from the opening 24, and parallel to the longitudinal axis of the shaft 14.

The light guide 30 is substantially rigid and has, for example, a metal sleeve in which optical fibers or another light-conducting medium (not shown) are contained.

At a proximal end 34, the light guide 30 has a coupling part 36 which cooperates with the coupling part 18 of the shaft 14 to secure the light guide 30 on the shaft 14. The coupling part 18 and the coupling part 36 together preferably form a plug coupling, so that when the light guide 30, which is withdrawable from the shaft 14, is reinserted into the shaft 14, it can be secured on the shaft 14 by simply plugging together the coupling parts 18 and 36. The plug coupling is designed such that the light guide 30 can be coupled to the shaft 14 only in a specific position of rotation about its own longitudinal axis.

Moreover, the light guide 30 has, at the proximal end, a connector 38 for attachment of a fiber optic cable (not shown) via which light from an external light source can then be fed to the light guide 30.

As can be seen from FIG. 1, a light-emitting distal end 40 of the light guide 30 is angled relative to the longitudinal axis 12 of the shaft 14, specifically by an angle in the range of about 70° to about 110°. In the preferred illustrative embodiment shown, the light-emitting distal end 40 of the light guide 30 is angled by 90° relative to the longitudinal axis 12 of the shaft 14. A light-emitting window 42 of the light-emitting distal end 40 extends in particular approximately parallel to the longitudinal axis 12 of the shaft 14.

As has already been mentioned, the light guide 30 can be withdrawn from the shaft 14. FIG. 4 shows the reverse procedure, in which the light guide 30 has just been inserted into the shaft 14. The light guide 30 is inserted into the shaft 14 until the coupling parts 18 (shaft 14) and 36 (light guide 30) are in engagement with one another, as is shown in FIG. 1.

Figure 5:
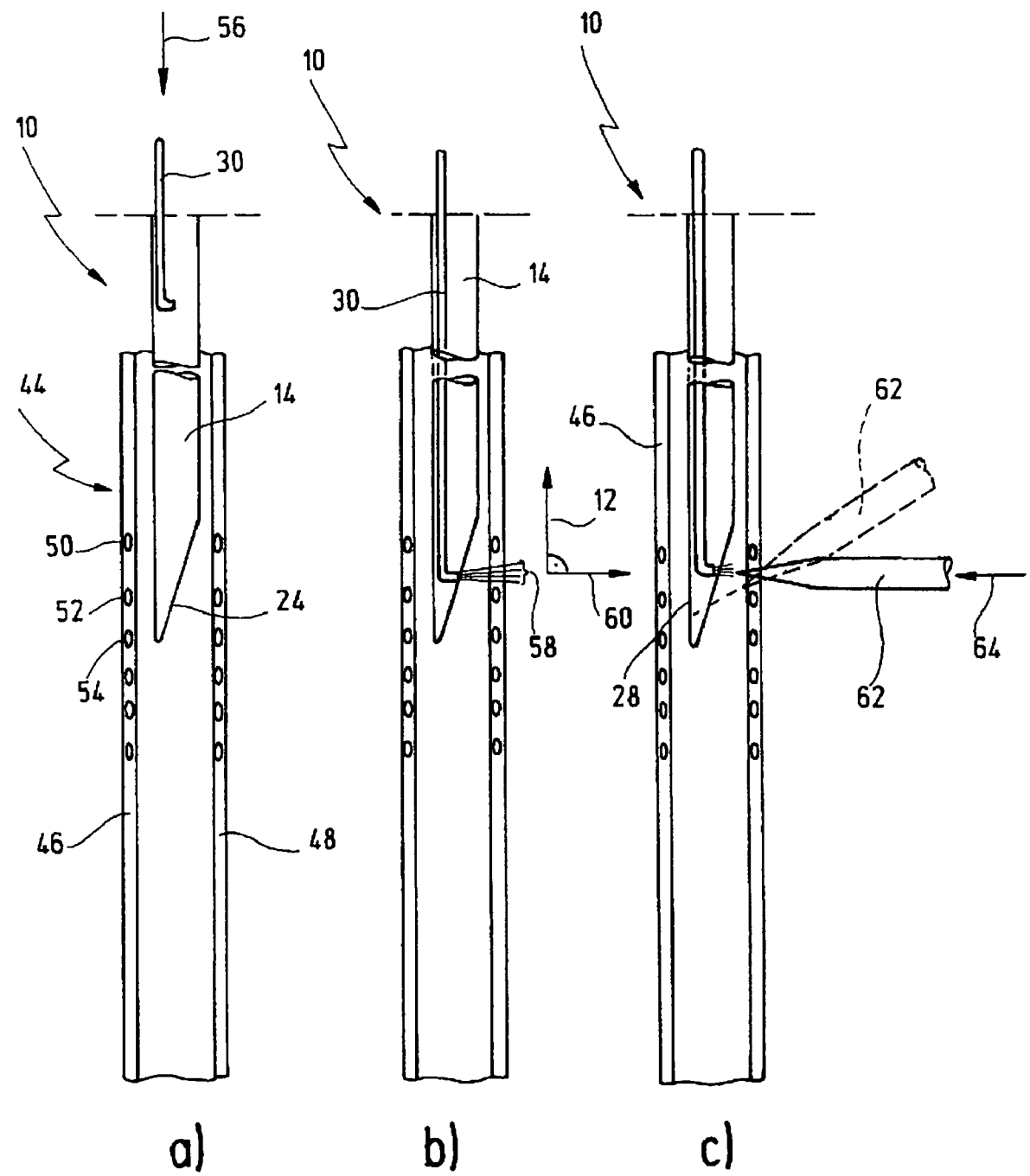
FIGS. 5a) to c) show schematic representations of three method steps involved in the use of the endoscope from FIG. 1 in the context of a tracheotomy.

FIGS. 5a) to c) are schematic representations showing the use of the endoscope 10 in the context of a tracheotomy.

Reference number 44 designates a patient's trachea, shown in a stylized form.

A posterior wall 46 of the trachea, directed toward the back of the patient's throat, and an anterior wall 48 of the trachea, directed toward the larynx, are shown in a stylized form in the drawing. Cricoid cartilages or tracheal rings 50, 52, 54, etc., are situated in the tracheal wall 46, 48.

In a first method step, shown in FIG. 5a), the endoscope 10 with the shaft 14 is introduced through the mouth and throat into the trachea 44, and specifically to the extent that the opening 24 of the shaft 14 comes to lie more or less level with the first cricoid cartilages 50 to 54 and points in the direction of the anterior wall 48 of the trachea. In cases where the light guide 30 has not been fitted into the shaft 40 upon insertion of the endoscope 10, the light guide 30 is introduced into the shaft 14 in the direction of the arrow 56, specifically until the light-emitting distal end, which, as has been described above, is angled relative to the longitudinal axis 12 of the shaft 14 by about 90°, comes to lie level with the opening 24 and the window 42 points in the direction of the opening 24. This is shown in FIG. 5b). The exact position of the light-emitting distal end 40 of the light guide 30 is shown in FIG. 1, and it will be noted that the light-emitting window 42 is situated in the proximal area of the opening 24 in the final position of the light guide 30 in the shaft 14.

If the light guide 30 is now supplied with light, the light emerges from the window 42 of the light guide 30 and produces a preferably sharply defined light spot 58 of small size on the anterior wall 48 of the trachea, which light spot shows through the patient's skin and can thus be seen from outside. The size of the light spot 58 is shown purely schematically in FIG. 5b), and in particular said light spot 58 can also cover the first cricoid cartilage 50 and the second cricoid cartilage 52, such that these are discernible by way of the light spot, on account of the different intensity of these light spot regions occasioned by the cricoid cartilages 50 and 52. As is shown in FIG. 5b), the light propagation direction 60 is substantially perpendicular to the longitudinal axis 12 of the shaft 14 of the endoscope 10.

According to FIG. 5c), the sharply defined light spot 58 can now be used, with the aid of a trocar 62 placed on the light spot 58 showing through the patient's skin, to make a precisely targeted incision through the skin and then through the anterior wall 48 of the trachea, without damaging the cricoid cartilages 50, 52, 54, etc.

By virtue of the oblique formation of the opening 24 that runs toward a point, and by virtue of the resulting large surface area of the rear wall 28 of the shaft 14 in the region of the opening 24, the trocar 62, when advanced farther in the direction of an arrow 64, strikes the rear wall 28, and the rear wall 28 thus reliably ensures that the posterior wall 46 of the trachea is not also pierced.

FIG. 5c) also shows clearly that, even when the trocar 62 is inserted obliquely, as is indicated by broken lines, the trocar 62 is still effectively stopped by the rear wall 28 of the opening 24 and cannot damage the posterior wall 46 of the trachea.

In subsequent method steps too, in which further instruments are introduced through the incision created with the trocar 62, the rear wall 28 safely protects the posterior wall 46 of the trachea from injury.

What is claimed is:

1. An endoscope, comprising
an elongated tubular shaft for introducing into a body of a patient, said shaft having a longitudinal axis and a distal end, and further having an opening at said distal end, said opening having a proximal end and a distal end and said opening of said shaft extending obliquely relative to said longitudinal axis of said shaft,
a light guide arranged along said shaft and having a light-emitting distal end, said light-emitting distal end being arranged closer to said proximal end of said opening than said distal end of said opening in order to radiate light from a proximal area of said opening,
said light-emitting distal end of said light guide being angled relative to said longitudinal axis of said shaft by an angle in a range of about 70° to about 110°.

2. The endoscope of claim 1, wherein said light-emitting distal end of said light guide comprises a light-emitting window which extends approximately parallel to said longitudinal axis of said shaft when said light guide is oriented parallel to said longitudinal axis of said shaft.

3. The endoscope of claim 1, wherein said light-emitting distal end of said light guide is angled relative to said longitudinal axis of said shaft by an angle in a range of about 80° to about 100°.

4. The endoscope of claim 1, wherein said light-emitting distal end of said light guide is angled relative to said longitudinal axis of said shaft by an angle of about 90°.

5. The endoscope of claim 1 wherein an edge of said opening forms, with said longitudinal axis of said shaft, an angle in a range of about 10° to about 40°.

6. The endoscope of claim 5, wherein said edge of said opening forms, with said longitudinal axis of said shaft, an angle in a range of about 15° to about 25°.

7. The endoscope of claim 1, wherein said light guide can be arranged in an interior of said shaft, and wherein said light guide extends near a shaft wall of said shaft which is directed away from said opening.

8. The endoscope of claim 1, wherein said light-emitting distal end of said light guide has such a length that it does not protrude from said opening.

9. The endoscope of claim 1, wherein said light guide can be withdrawn from said shaft.

10. The endoscope of claim 1, wherein a coupling is present at a proximal end of said light guide and at a proximal end of said shaft for the purpose of securing said light guide on said shaft in a predetermined position of rotation of said light guide relative to said shaft.

11. The endoscope of claim 1, used in a tracheotomy, wherein said opening of said shaft is sized to form a protective surface, which prevents a trocar from piercing the posterior wall of the trachea.

12. An endoscope, comprising
- an elongated tubular shaft for introducing into a body of a patient, said shaft having a longitudinal axis and a distal end, and further having an opening at said distal end, said opening having a proximal end and a distal end and said opening of said shaft extending obliquely relative to said longitudinal axis of said shaft, said opening forming an angle in a range of about 10° to about 40° with said longitudinal axis of said shaft,
- a light guide arranged along said shaft and having a light-emitting distal end, said light-emitting distal end being arranged closer to said proximal end of said opening than said distal end of said opening in order to radiate light from a proximal area of said opening.

13. The endoscope of claim 12, wherein said edge of said opening forms, with said longitudinal axis of said shaft, an angle in a range of about 15° to about 25°.

14. The endoscope of claim 12, wherein said light-emitting distal end of said light guide comprises a light-emitting window which extends approximately parallel to said longitudinal axis of said shaft when said light guide is oriented parallel to said longitudinal axis of said shaft.

15. The endoscope of claim 12, wherein said light guide can be arranged in an interior of said shaft, and wherein said light guide extends near a shaft wall of said shaft which is directed away from said opening.

16. The endoscope of claim 12, wherein said light-emitting distal end of said light guide has such a length that it does not protrude from said opening.

17. The endoscope of claim 12, used in a tracheotomy, wherein said opening of said shaft is sized to form a protective surface, which prevents a trocar from piercing the posterior wall of the trachea.

\* \* \* \* \*